United States Patent [19]

Rehder

[11] Patent Number: 4,865,606
[45] Date of Patent: Sep. 12, 1989

[54] ENDOPROSTHESIS FOR A KNEE-JOINT

[75] Inventor: Günther Rehder, Kiel, Fed. Rep. of Germany

[73] Assignee: Friedrichsfeld GmbH Keramik und Kunststoffwerke, Mannheim, Fed. Rep. of Germany

[21] Appl. No.: 230,883

[22] Filed: Aug. 11, 1988

[30] Foreign Application Priority Data

Aug. 13, 1987 [DE] Fed. Rep. of Germany ....... 3726969

[51] Int. Cl.$^4$ .............................................. A61F 2/38
[52] U.S. Cl. ..................................................... 623/20
[58] Field of Search ..................................... 623/18–21

[56] References Cited

U.S. PATENT DOCUMENTS

| 4,085,466 | 4/1978 | Goodfellow et al. | 623/20 |
| 4,112,522 | 9/1978 | Dadurian et al. | 623/20 |
| 4,216,549 | 4/1978 | Hillberry et al. | 623/20 |
| 4,262,368 | 4/1981 | Lacey | 623/20 |
| 4,462,120 | 7/1984 | Rambert | 623/20 |
| 4,790,853 | 12/1988 | Eugelbrecht | 623/20 |

FOREIGN PATENT DOCUMENTS

| 2550704 | 5/1976 | Fed. Rep. of Germany . |
| 2636816 | 2/1977 | Fed. Rep. of Germany . |
| 2452412 | 11/1977 | Fed. Rep. of Germany . |
| 3528204 | 2/1985 | Fed. Rep. of Germany . |
| 1553836 | 10/1979 | United Kingdom . |
| 2088724 | 6/1982 | United Kingdom | 623/20 |

OTHER PUBLICATIONS

Maquet, *Biomechanics of the Knee*, Springer-Verlag, Berlin, Heidelberg, New York, (1976), pp. 32–39.

Primary Examiner—Richard J. Apley
Assistant Examiner—James Prizant
Attorney, Agent, or Firm—Foley & Lardner, Schwartz, Jeffery, Schwaab, Mack, Blumenthal & Evans

[57] ABSTRACT

An endoprosthesis for a knee joint comprising a femur part (6), a tibia part (8), and a middle part (18) which is articulated on the femur part (6) by a pin (14). The middle part (18) is pivotable with respect to the tibia part (8) about a centering pin (20), and a stop is pivoted which is dependent on the flexion angle. A bearing part (54), acting as artificial meniscus, is arranged between the femur part (6) and the middle part (18), and has a first guide element (56) coaxial to the flexion axis and in engagement with the bearing member (58) of the femur part (6). The bearing part (54) is displaceable with respect to the middle part (18) and also comprises a second guide element (60) in engagement with a guide track (62) of the middle part (18); the pin (14) is arranged eccentric to the bearing member (58), and movement of the flexion axis is forced along an evolute curve. The invention avoids localized load peaks while accomplishing the physiological functions of the knee joint during movement and load.

21 Claims, 3 Drawing Sheets

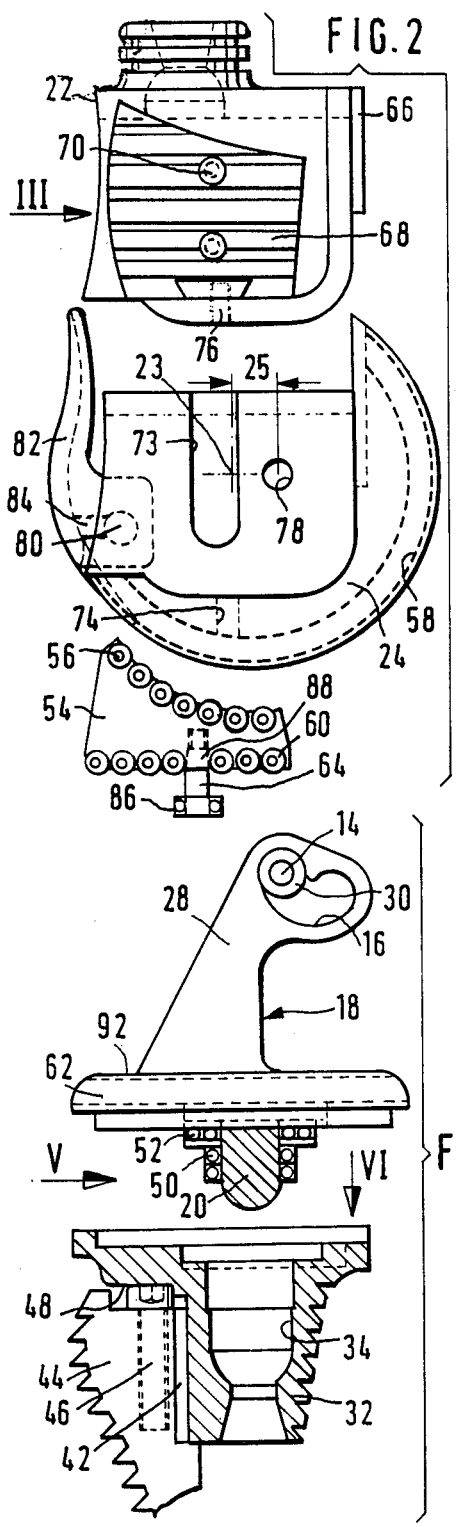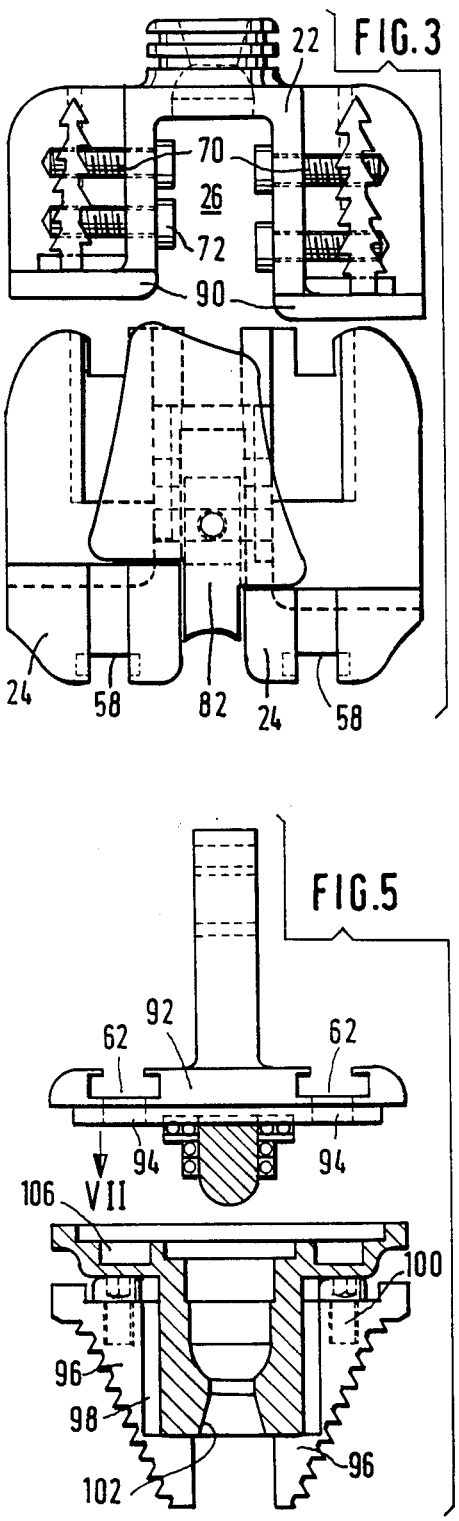

ENDOPROSTHESIS FOR A KNEE-JOINT

BACKGROUND OF THE INVENTION

The present invention relates to an endoprosthesis for a knee joint having a femur part, a tibia part and a middle part which is movably connected to the femur part via a preferably horizontally arranged pin, wherein the femur part is pivotable with respect to the tibia part about an essentially horizontal flexion axis and has a curved bearing member and also a centering pin is arranged between the middle part and the tibia part, about which centering pin the middle part is pivotably mounted with respect to the tibia part, and furthermore having a stop, which is dependent on the flexion angle, for the femur part whose pivoting movement with respect to the centering pin is limited in the extended position.

U.S. Pat. No. 4,112,522 discloses an endoprosthesis of the foregoing general type having a femur part, an intermediate part and a tibia part which has a range of movement about the flexion axis of $-5°$ to $+145°$. The rotation of the lower leg is controllable by means of the flexion axis pin whose middle area forms a stop, which is dependent on the flexion angle, for the pivoting movement of the centering pin which is rotationally fixedly connected to the tibia part. In addition, the middle part is designed as an eccentric rotational element which bears in a recess of the centering pin, the pin axis being spaced a distance from the flexion axis and being arranged essentially at a right angle to the latter. The middle part has bearing surfaces, coaxial to the flexion axis, for similarly coaxial bearing bushes on the femur part. The defined specification of the flexion axis independent of the flexion angle does not correspond to physiological kinematics. There is a risk of very high and unacceptable peak loads occurring as a result of the contact of the bearing surfaces between femur part and tibia part being only in line-form and, in extreme cases, even in point-form. Such peak loads are disadvantageous with respect to durability and operational capacity.

In the book *Biomechanics of the Knee*, Paul G. J. Maquet, Springer-Verlag, Berlin, Heidelberg, New York (1976), the construction and the functioning of the knee joint are described in detail. On pages 32 to 39 in particular of this book, with reference to FIG. 35, the displacement of the flexion axis in dependence on the flexion angle is explained in detail. A simple hinge movement between femur part and tibia part does not satisfy these special physiological kinematics and statics, for which reason considerable difficulties have arisen in the past as regards operational reliability, durability, load capacity, etc.

U.S. Pat. No. 4,085,466 discloses a knee joint endoprosthesis in which two artificial meniscus elements are arranged between the curved bearing surfaces of the femur part and the essentially flat bearing surfaces of the tibia part. No restraint is provided for the artificial meniscus elements, and instead an automatic alignment is effected by means of the ligaments and muscles. The curved bearing surfaces and also the meniscus elements require a high production cost, and as a result of work tolerances, high surface pressures are difficult to avoid in practice. Moreover, a fully functional locomotion apparatus is required, so that, in the event of any serious damage to the latter, it is not at all possible for the endoprosthesis to be used. In order to permit mutual rotation of femur and tibia on extending and flexing, the arcuate bearing surfaces of the femur part and of the two meniscus elements must be spherically curved, for which reason a considerable production cost is necessitated. Even slight deviations in the geometry of the bearing surfaces can lead to high surface pressures and peak loads, which result in rapid wear and damage. The use of special, nonrigid materials for the meniscus element necessitates additional measures and, nonetheless, a high production outlay for the bearing surfaces.

West German Offenlegungsschrift No. 24 52 412 discloses an endoprosthesis whose femur part has trough-like, arcuate rolling surfaces. The radius of curvature of these rolling surfaces decreases in the dorsal direction. Two intermediate elements, which have spherically curved bearing surfaces for the rolling surfaces of the femur part, are arranged fixedly and nondisplaceably on the tibia part. The rolling surfaces of the femur part bear on the bearing surfaces of the tibia part only over a small portion of the total area, so that again in this case high surface pressures must be expected. The pivoting between femur part and tibia part is made possible by the spherical design of the surfaces, but this necessitates a not inconsiderable production cost.

SUMMARY OF THE INVENTION

It is the object of the present invention to provide an improved endoprosthesis for a knee joint.

A further object of the invention is to provide an endoprosthesis for a knee joint in which the physiological knee joint functions are fulfilled during movement and load.

It is also an object of the present invention to provide an endoprosthesis for a knee joint in which forces are transferable on as large surfaces as possible, and localized load peaks, due in particular to line or point contact, are avoided.

Another object of the present invention is to provide an endoprosthesis for a knee joint which has small dimensions and which additionally assures proper physiological kinematics and statics independently of the functional capacity of ligaments and muscles.

An additional object of the present invention is to provide an endoprosthesis in which good tribologic characteristics as regards the mutually movable parts and a high static rigidity of the force-transmitting parts are assured.

A still further object of the present invention is to provide an endoprosthesis for a knee joint in which frictional forces between the mutually movable individual components are minimized, in particular with regards to static friction at the start of a movement.

These and other objects of the invention are achieved by providing an endoprosthesis for a knee joint, comprising a femur part, a tibia part, a middle part movably connected to the femur part via a pin, a centering pin arranged between the middle part and the tibia part about which the middle part is pivotably mounted with respect to the tibia part, and a stop for the femur part whose pivoting movement with respect to the centering pin is limited in the extended position, said stop being dependent on the flexion angle, said femur part being pivotable with respect to the tibia part about an essentially horizontal flexion axis and having a curved bearing element; wherein a bearing part, which acts as an artificial meniscus, is arranged between the femur part and the middle part, said bearing part being displaceable with respect to the middle part in a plane orthogonal to the centering pin and having a first guide element engaging the bearing element of the femur part and a second guide element engaging a guide track of the middle part, and wherein said pin is arranged eccentric to the center axis of the bearing member of the femur part in such a way that, upon flexing, the flexion axis is movable along an evolute curve.

In accordance with the invention, a bearing part, designed as artificial meniscus, is arranged between the femur part and the tibia part, in particular on the middle part, the bearing part has a first guide element which is coaxial to the flexion axis and which engages a guide member of the femur part, the meniscus part is arranged displaceably with respect to the middle part in a plane which is essentially orthogonal to the centering pin, the bearing part also has a second guide element which engages a guide track of the middle part, and when the joint is flexed, the pin is guided along a guide which is preferably designed as an elongated hole or slot and/or corresponds to an evolute curve.

The proposed endoprosthesis has a secure and compact construction and assures optimum achievement of the physiological kinematics and statics, with localized load peaks being reliably avoided. By means of the proposed bearing part, the movement paths are divided, on the one hand, into a purely rotational movement by means of the first guide element, and, on the other hand, into purely translational movement by means of the second guide element.

Another important feature is the movement of the flexion axis along an evolute path by means of the pin being guided in particular in an elongated slot or the like, so that during the flexing, the displacement of the bearing part is forced to occur, and a continuous contact of the two guide elements with the bearing member is assured. According to the invention, the pin is arranged eccentric to the circular bearing member which is advantageously designed as a cylindrical bearing track. As a result of the offsetting of the axis according to the invention, the bearing part is forced to follow through in conjunction with the guide of the pin during flexing. The guide is preferably designed as an evolutely curved slot, but, within the scope of the invention, the guide can also be designed as a straight elongated slot, groove or the like, in order to permit axis compensation according to the invention during flexing.

Although the pin is advantageously arranged on the femur part and the guide on the middle part or tibia part, within the scope of the invention the reverse arrangement can also be provided in a corresponding manner. According to the invention the bearing track is designed as a circle, in particular in the form of a cylinder, and the pin is arranged eccentric to the bearing track. As a result of the eccentric articulation according to the invention of the middle part and its guide, during flexing the displacement of the bearing part is compelled to occur by means of the guide in order to effect axis compensation. A rolling/sliding movement thereby takes place which can advantageously be limited by means of the guide to a predeterminable flexion angle range, whereupon, subsequently, only a rolling movement takes place and the translational movement does not occur and, where appropriate, may also be effected in the opposite direction. Particularly as a result of the shape and the size of the recess, which is preferably designed as an elongated slot, the limit of the angle range for rotational/translational movement can be preset to the desired angle, which lies in particular between 85 and 95 degrees. In order to minimize friction, the guide elements are advantageously designed as roller bearings. The bearing member and the bearing track of the femur part and/or the guide track of the middle part are advantageously designed as undercut grooves into which the guide elements correspondingly engage so that tensile loads and pressure loads are absorbed in an operationally reliable manner. Within the scope of the invention the guide elements can be arranged on the femur part or on the middle part, while the bearing part correspondingly is provided with the coaxial bearing track and/or the guide track.

In one preferred embodiment, the bearing part comprises at least one pin engaging in a control path of the tibia part, or vice versa, for forming the stop which is dependent on the flexion angle. If, for example, the pin is arranged on the bearing part, then during the translational movement of the bearing part, the pin is also moved. The control path is designed in such a way that, in the extended position, a pivoting movement of the tibia part is blocked and, as the flexion angle increases the pivoting angle of the tibia part also increases.

In accordance with another preferred embodiment, the femur part comprises an intracondylar cage and also two laterally arranged condyle rolls, with the guide members or bearing tracks for the first guide element. The cage has an approximately U-shaped cross-section opening towards the tibia part. A connecting rod according to the invention can be passed through the opening located in the middle of the cage for anchoring in the femur. Moreover, the cage is secured in the condyle by means of compression plates, with the screwing being carried out by way of the central opening. The tibia part also advantageously comprises a cage which is secured by means of a connecting rod and a screw element screwed into the cortical matter. The connecting rod for the tibia cage and also the connecting rod for the intracondylar cage bear by means of spherical surfaces on likewise spherical surfaces in the openings of the cages. By this means, an axis compensation can be effected without difficulty. The screw element advantageously has, on its outer surface, a self-tapping thread which is preferably designed as a buttress thread. The connecting rod is screwed into an inside thread with a stop in such a way that following the complete screwing-in, when the connecting rod is pivoted, the screw element is also pivoted and thus screwed into the cortical matter. Within the scope of the invention the tibia part is also anchored in a corresponding manner. Within the scope of this invention, this method of fixing joint parts can also be employed for joints other than the described endoprosthesis, in particular the hip joint. Alternatively, the femur part and tibia part can also be cemented in place in the customary manner.

In one advantageous embodiment the tibia cage is supported in the cortical matter by at least one anchoring claw. This anchoring claw is displaceable in a preferably dovetail-shaped guide track of the cage, a pressure screw assuring the distance to the cage and, consequently, a good pressure seating in the cortical matter.

Within the scope of this invention, the described anchoring of the cages by means of compression plates or anchoring claws and connecting rods can be provided, not only for a knee joint, but correspondingly also for a hip joint. In both cases of use a reliable anchoring of the joint parts is assured. By means of the described anchoring claws and the screws, the cage can be adjusted in an optimum manner with respect to the bone. Furthermore, by means of different sizes and shapes of the anchoring claws, adaptation to the particular conditions can be carried out in a simple manner even during operations, whereby a functionally reliable anchoring is nonetheless assured.

BRIEF DESCRIPTION OF THE DRAWINGS

The invention will be explained in further detail with reference to illustrative embodiments shown in the accompanying drawings, in which:

FIG. 2 shows an exploded presentation of the femur part, and more especially of the intracondylar cage and a condyle roll, and also of the bearing part;

FIG. 3 shows a side view of the intracondylar femoral cage and the two condyle rolls viewed in the direction of the arrow III shown in FIG. 2;

FIG. 4 shows an exploded presentation of the middle part and also of the tibial cage;

FIG. 5 shows a view in viewing direction V according to FIG. 4;

DETAILED DESCRIPTION OF PREFERRED EMBODIMENTS

Figure 1:
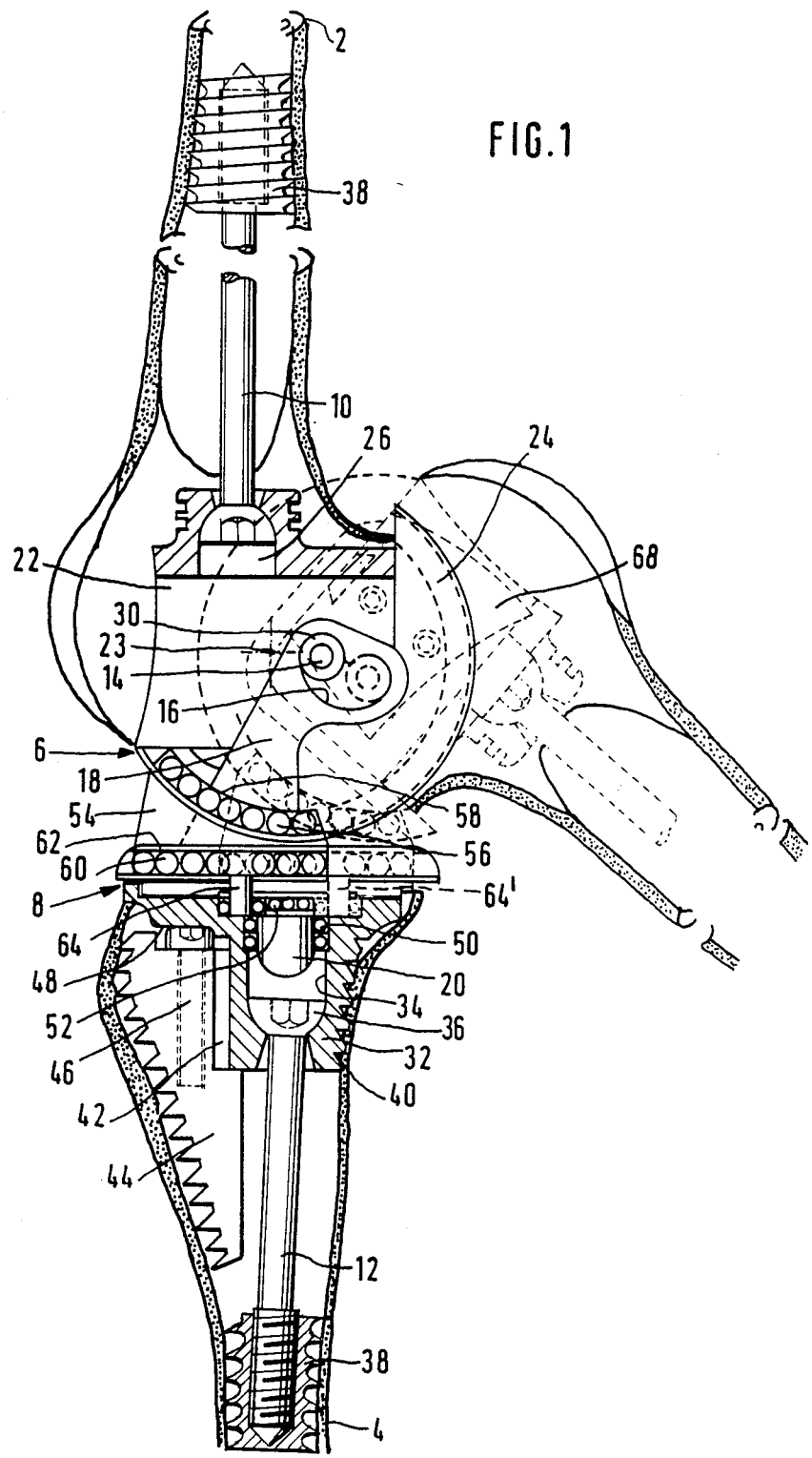
FIG. 1 shows a longitudinal section of the knee joint endoprosthesis in the extended position and in the maximum flexion position.

FIG. 1 shows part of the femur 2 and tibia 4 into which the femur part 6 and the tibia part 8 are anchored respectively by means of connecting rods 10 and 12. The femur part 6 comprises a pin 14 which is guided in a recess 16 formed as an elongated slot in a middle part 18. The middle part 18 has a centering pin 20 engaging in the tibia part 8, the rotation of the tibia part 8 and thus of the lower leg about this centering pin 20 being controlled in dependence on the flexion. In this respect, the illustrated design of the guide of the pin 14 in the recess 16, which is formed as an elongated slot, is not to be construed as limiting. Within the scope of the invention a straight elongated slot, a straight groove or even an elongated slot provided with a different curvature can be provided for guiding pin 14.

The femur part 6 comprises an intracondylar cage 22 and also two condyle rolls 24 arranged on both sides, with only the condyle roll lying behind the plane of the drawing being shown in this view. The condyle rolls are connected to the cage 22 by means of screws. According to the invention the condyle rolls 24 have circular curved bearing members, which will be described in detail hereinafter. These are advantageously designed as bearing tracks, preferably as parts of cylinder surfaces, which lie coaxial to a common center axis 23. This center axis 23 forms the flexion axis of the endoprosthesis, with the pin 14 being arranged according to the invention at a predetermined distance eccentric to the center axis 23. Thus, during flexing, there is a forced movement and displacement of the middle part which is articulated on the femur part via the pin eccentric to the flexion axis. The bearing part which will be described hereinafter, and which acts as artificial meniscus, forces a further movement. If the tibia part is considered as stationary, then as a result of the forced movement of the middle part via the eccentric pin in the femur part, a forced movement of the flexion axis is obtained along an evolute curve. According to the invention, by means of the shaping of the outer surface of the pin and/or of the geometry of the recess 16, the movement of the flexion axis is forced along an evolute curve corresponding to the physiological movement path. No spherical bearing tracks, through which the forces exerted on the endoprosthesis are transmitted, are required for this purpose. The recess 16 in the form of an elongated slot and the engaging pin do not serve for force transmission, but for the forcible control and movement of the middle part 18 and of the bearing part 54. The cage 22 is of approximately U-shaped design and comprises, in the middle, an opening 26 which opens downwards towards the tibia part and into which the middle part 18 projects according to the invention with an arm 28. The elongated slot 16 is arranged at the upper end of this arm 28, with the pin 14 fixed in the cage 22 being guided by means of a bearing 30, which is schematically illustrated. According to the invention this elongated slot 16 is curved in such a way that, upon flexing of the joint, the flexion axis executes the previously described evolute movement with respect to the tibia part. The maximum bending position is indicated by broken lines.

The tibia part 8 comprises a tibial cage 32 which has, in the middle, a bore 34 with a spherical bottom. The screw head of the tibial connecting rod 12 (and the same applies to the femoral connecting rod 10 and the intracondylar cage 22) has a correspondingly spherically designed bearing surface, so that an axis compensation can be effected. The other end of the connecting rod 12 is screwed into a screw element 38 which has, on its outer surface, a self-tapping thread for anchoring in the tibia. The cage 32 has, on one side, claws 40 which engage firmly in the inside face of the tibia 4. On the opposite side, the cage 32 comprises a guide groove 42, designed as a dovetail, for an anchoring claw 44 into which a pressure screw 46 is screwed, in particular by means of left-hand threading. The head of this pressure screw 46 bears against the bottom of a shoulder 48 of the tibia part and, as a result of the left-hand threading, when the pressure screw 46 is turned in clockwise direction the distance between the shoulder 48 and the anchoring claw 44 is increased. As will be explained further hereinafter, two further anchoring claws which are diametrically opposite each other are correspondingly provided in front of and behind the plane of the drawing. According to the invention, a secure fixing of the cage 32 can be effected by means of these anchoring claws, the necessary alignment and contact pressure being achieved by means of the pressure screws.

The centering pin 20 is fixedly connected to the middle part 18 and projects into the bore 34 of the tibial cage 32. Ball bearings 50 and 52 are provided as the radial and axial bearings, respectively, in order to achieve low-friction mounting. Furthermore, on the middle part 18, a bearing part 54 is in each case arranged displaceably on both sides of the arm 28. These bearing parts 54 are designed as artificial meniscus and are displaceable in a plane which is parallel to the flexion axis and orthogonal to the axis of the centering pin 20. Each bearing part 54 has a first guide element 56, which is designed here as a ball bearing and engages in the bearing member 58, designed as a bearing track, of the femur part and condyle roll 24. The guide element 56 according to the invention is arranged coaxial to the flexion axis, as is the associated bearing track 58. On the underside, the bearing part 54 has a second guide element 60 which is likewise designed as a roller bearing, i.e. ball bearing or rolling contact bearing, and engages in the guide track 62 of the middle part. A further important feature is that the bearing track 58 and the guide track 62 are in each case designed as undercut grooves, by which means lifting is prevented. In the illustrated extended position, the artificial meniscus or bearing part 54 is located on the other side of the axis of rotation defined by the centering pin 20 from the pin 14 which defines the flexion axis. As shown by the broken lines, the bearing part 54 is moved toward the right of the drawing as a result of the pin 14 being guided in the described elongated slot 16 during flexing. The pin 64", which is arranged on the underside of the bearing part, is thereby brought into the position indicated by 64"'. For the purpose of illustrating interrelationships, the pin 64 is shown completely in the drawing, although it is in actual fact arranged behind the section plane or drawing plane which runs through the center of the centering pin 20.

FIG. 2 shows, in an exploded presentation, the intracondylar cage 22, one of the two condyle rolls 24 and the bearing part 54 which forms an artificial meniscus. The cage 22 is provided with compression plates on a dovetail guide 66. In order to secure the compression plates 68, two screws 70 are screwed into corresponding threads in the compression plates, the screw heads engaging in a groove 73 of the condyle roll for the purpose of guiding and securing.

The condyle roll is attached to the cage 22 by means of a screw which engages through a bore 74 of the condyle roll 24 into a thread 76 in the bottom of the cage 22.

The condyle roll 24 furthermore comprises an eccentric bore 78 for receiving the above-mentioned pin which engages in the recess or elongated slot of the middle part. The condyle roll 24 comprises a shaft 80 for adjustably mounting the patella slide bearing 82, with the fixing being carried out by means of a screw 84 after the positioning. The bore 78 is at different distances from the individual points of the circular bearing track 58, and, by means of the articulation of the middle part via the pin, during flexion the follow-up is effected for the purpose of compensating the offsetting of the axis. The bearing track 58 and also the guide elements 56 are coaxial to the common center axis 23, with respect to which the bore 78 is eccentrically arranged. There is, therefore, an eccentric articulation of the middle part with respect to the center axis 23 which defines the flexion axis, so that, according to the invention, during flexion a controlled movement of the middle part 18 takes place in dependence on the flexion angle. Depending on the distance 25 of the bore 78, and thus of the pin, from the center axis 23 and on the configuration either of the outer surface of the pin or of the recess, an evolute movement of the flexion axis is effected.

The bearing part 54 engages in the bearing track 58 by means of its first guide element 56 which in accordance with the invention comprises a number of roller bearings which, like the bearing track 58, are arranged coaxial to the bore 78. Furthermore, the second guide elements 60 are designed as roller bearings, i.e. ball bearings or rolling contact bearings or needle bearings. The pin 64 also is provided at its free end with a ball bearing 86 so that, overall, a substantially frictionless guide is made possible. According to the invention, the pin 64 comprises a conical collar 88 in order to secure it against rotation. If desired, other means could also be provided for securing the pin 64 in the bearing part 54.

FIG. 3 shows the cage 22 and the condyle rolls 24 viewed in the direction of arrow III shown in FIG. 2. The approximately U-shaped design of the cage 22 can be clearly seen, with the middle opening 26 through which the screws 70 are screwed. The screw heads 72 are also shown, which are guided and secured by engagement in the grooves 73 of the two condyle rolls 24. The lower edges of the cage 22 have a height offset 90 corresponding to the anatomical height offset of the condyles. Each of the two condyle rolls 24 according to the invention comprises a bearing track 58, which is designed as an undercut groove and forms the femoral rolling or sliding track.

FIG. 4 shows the middle part 18 and the tibial cage 32, viewed in the same viewing direction as in FIG. 2. The rolling curve according to the invention in the form of the elongated slot 16 can be clearly seen at the top end of the arm 28. The pin 14 is guided in this rolling curve by means of the schematically illustrated ball bearing 30. The guide track 62 in the horizontal plate or plateau 92 of the middle part 18 is indicated by broken lines. Arranged on the centering pin 20 for radial and axial bearing are the two ball bearings 50 and 52 which run in the bore 34 of the tibial cage 32 over corresponding, oppositely facing bearing surfaces. The axial distance to the anchoring claw 74 can be preset according to the invention by means of the pressure screw 46. By means of the guide, which is formed as an elongated slot 16, during flexion the follow-up movement of the middle part 18 and of the bearing part 54 is forced to occur. A rolling movement is thereby effected and, at the same time, also a sliding translational movement. Within the scope of the invention, this combined rolling/sliding movement can be limited to a maximum flexion angle on the order of magnitude of about 90 degrees, advantageously between 85 and 95 degrees. For larger flexion angles only a rotational movement is then effected, whereby if desired, the middle part 18 may also execute a translational movement contrary to the original movement. The critical angle prescribed in this way is predetermined by the shape and, in particular, by the length of the elongated slot 16 or, in general, of the guide of the pin 14.

FIG. 5 shows the middle part 18 and the tibial cage 32 in viewing direction V. The two guide tracks 62 are now arranged for the two bearing parts according to the invention. According to the invention, the guide tracks 62 are each associated with an elongated slot 94 extending in the same direction and through which passes that pin of the bearing part which engages in the control path of the tibial cage. The two other anchoring claws 96 lying diametrically opposite each other can now also be seen. Claws 96 are likewise guided in dovetail guides 98 of the tibial cage 32. The pressure screws 100 likewise have a left-hand thread and are used for altering the distance and for bracing the anchoring claws 96 in the bone.

Figure 6:
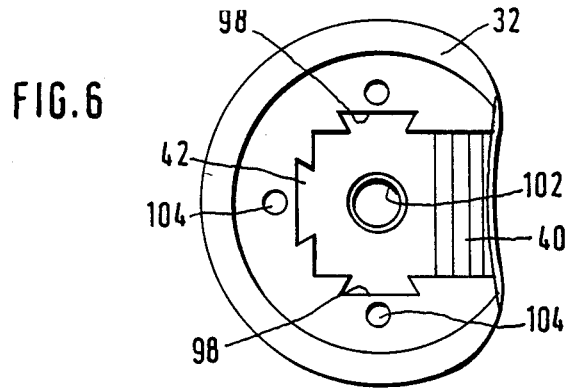
FIG. 6 shows a view of the tibial cage in viewing direction VI according to FIG. 4.

FIG. 6 shows a view of the tibial cage in viewing direction VI according to FIG. 4, and more especially without the anchoring claws. The guide grooves 42 and 9B, designed here in the form of dovetails, can be seen, as can the claws 40 for direct contact with the inner wall of the bone. Within the scope of the invention, the bore 102 may be formed conically in order to permit the axis compensation via the associated connecting rod. The through bores 104 are provided for the wrench used to turn the pressure screws of the anchoring claws.

Figure 7:
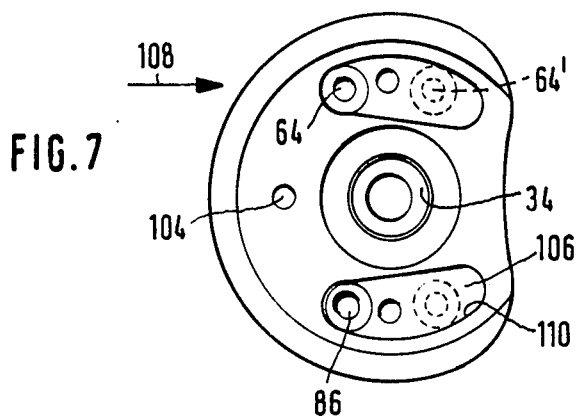
FIG. 7 shows a top view of the tibial cage in viewing direction VII according to FIG. 5, with the pins of the bearing part also indicated.

FIG. 7 shows a view of the tibial cage 32 in viewing direction VII according to FIG. 5, with the two control paths 106 for the pins of the respective bearing parts now also being clearly seen. The ball bearings 86 are also shown for the purpose of illustrating the interrelationships. In the extended position the two ball bearings 86 in the respective control path 106 assume the end position toward the left of the drawing and, by means of the stop thus formed, a pivoting of the tibial cage 32 about the axis vertical to the plant of projection is blocked. According to the invention, during flexion the two bearing parts and, consequently, also the pin 64 with the bearings 86 execute in each case a translational movement perpendicular to the centering pin, as is indicated by the arrow 108. In the maximum flexion position the two pins have assumed the position indicated by the broken line 6 and now permit the rotation of the tibia part about an angle of approximately 15°. The two control pats 106 are cut out of the tibia part 32 from above, with the outer edges 110 lying coaxial to the bore 34.

Figure 8:
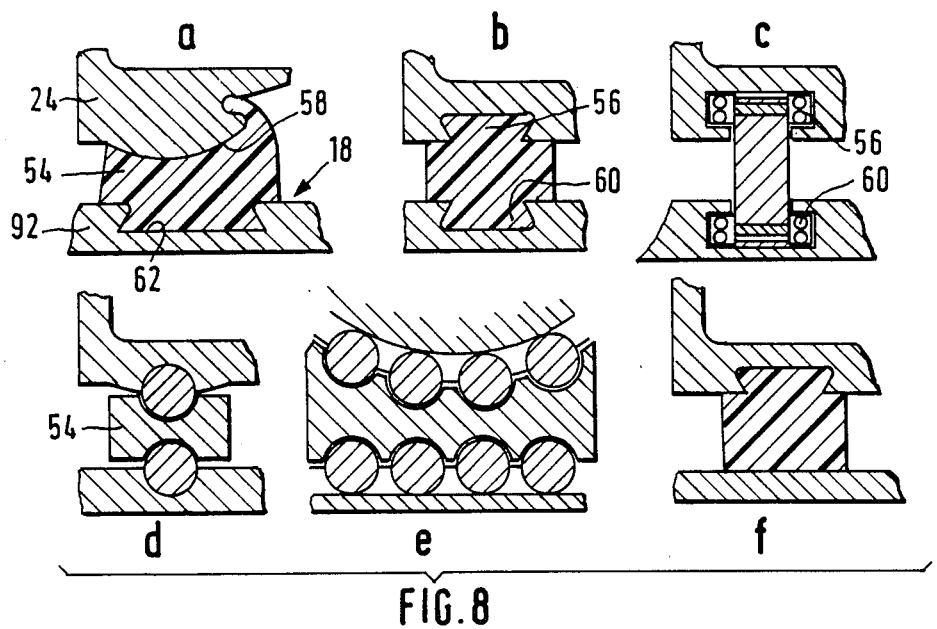
FIGS. 8a-f show various embodiments of the guides of the bearing parts with respect to the condyle roll and the middle part using different materials.

FIG. 8 shows various designs of condyle roll 24, bearing part 54, middle part 18 and of the corresponding bearing and guide tracks 58 and 62 respectively, including the guide elements 56 and 60. The different designs can be selected depending on the materials employed. The embodiments according to FIGS. 8a, 8b and 8f are advantageously provided when the condyle roll and the middle part 18 or its plateau 92 are made of chromium/cobalt/titanium or ceramic. In this case the bearing part 54 will be made, at least at its surface and preferably throughout, of a synthetic material such as, in particular, polyethylene. The embodiments according to FIGS. 8c, d, e proves advantageous when using chromium/cobalt and titanium as the condyle roll and tibia plateau, whereby the bearing part 54 as a bearing block for ball bearings or needle bearings can be made of the same material.

The foregoing description has been set forth merely to illustrate the invention and is not intended to be limiting. Since modifications of the described embodiments incorporating the spirit and substance of the invention may occur to persons skilled in the art, the scope of the invention should be limited solely with reference to the appended claims and equivalents thereof.

What is claimed is:

1. An endoprosthesis for a knee joint, comprising a femur part (6), a tibia part (8), a middle part (18) movably connected to the femur part (6) via a pin (14), a centering pin (20) arranged between the middle part (18) and the tibia part (8) about which the middle part (18) is pivotably mounted with respect to the tibia part (8), and a stop for the femur part (6) whose pivoting movement with respect to the centering pin (20) is limited in the extended position, said stop being dependent on the. flexion angle, said femur part (6) being pivotable with respect to the tibia part (8) about an essentially horizontal flexion axis and having a curved bearing element (58); wherein a bearing part (54), which acts as an artificial meniscus, is arranged between the femur part (6) and the middle part (18), said bearing part (54) being displaceable with respect to the middle part (18) in a plane orthogonal to the centering pin (20) and having a first guide element (56) engaging the bearing element (58) of the femur part (6) and a second guide element (60) engaging a guide track (62) of the middle part (18), and wherein said pin (14) is arranged eccentric to the center axis (23) of the bearing member (58) of the femur part in such a way that, upon flexing, the flexion axis is movable along an evolute curve.

2. An endoprosthesis as claimed in claim 1, wherein said bearing member (58) of the femur part (6) and said first guide element (56) of the bearing part (54) are arranged coaxial to the center axis (23), and said pin (14) is arranged eccentrically to, and spaced a distance (25) from, said center axis.

3. An endoprosthesis as claimed in claim 1, wherein said stop which is dependent on the flexion angle is formed by at least one pin on one of the bearing part (54) and the tibia part (8) engaging in a control path (106) on the other of the bearing part and the tibia part.

4. An endoprosthesis as claimed in claim 1, wherein said guide track (62) of the middle part (18) is arranged essentially parallel to the flexion axis of the joint.

5. An endoprosthesis as claimed in claim 1, wherein said femur part (6) comprises an intracondylar cage (22) and two laterally arranged condyle rolls (24), each having a bearing member (58).

6. An endoprosthesis as claimed in claim 5, wherein said intracondylar cage (22) has a substantially U-shaped cross-section with an opening (26) open towards the tibia part (8).

7. An endoprosthesis as claimed in claim 5, wherein said intracondylar cage (22) is screwed and fixed by means of compression plates (68) inserted into slots in the condyle.

8. An endoprosthesis as claimed in claim 1, wherein said first and second guide elements (56, 60) comprise roller bearings.

9. An endoprosthesis as claimed in claim 1, wherein said centering pin (20) is pivotably mounted in the tibia part (8) by means of roller bearings.

10. An endoprosthesis as claimed in claim 9, wherein said roller bearings are axial and radial ball bearings (50, 52).

11. An endoprosthesis as claimed in claim 1, wherein at least one of said femur part (6) and said tibia part (8) has a cage (22, 32) having a bore for a connecting rod (10, 12) which bears, by means of a spherical bearing surface, on a corresponding surface of said cage (22, 32), and a free end of said connecting rod (10, 12) is screwed into a screw element (38) having a self-tapping external thread for anchoring in a bone.

12. An endoprosthesis as claimed in claim 11, wherein said cage (32) is secured in the bone by means of anchoring claws (44, 96).

13. An endoprosthesis as claimed in claim 11, wherein said cage (32) has anchoring claws (40) over at least part of its outer surface, said anchoring claws (44, 96) being guided in said cage (32) in guides (66, 98), and the spacing of the anchoring claws (44, 96) to the cage (32) is predeterminable by means of pressure screws (36, 100).

14. An endoprosthesis as claimed in claim 13, wherein said guides (66, 98) are dovetail guides.

15. An endoprosthesis as claimed in claim 1, wherein said middle part (18) carries said centering pin (20) on the underside of a plateau (92), and said centering pin (20) is mounted by means of bearings (50, 52) in a bore (34) of a tibial cage (32).

16. An endoprosthesis as claimed in claim 6, wherein said middle part (18) has an arm (28) received in the opening (26) of the intracondylar cage (22), and said arm has at an upper end thereof, a roll curve which is designed as an elongated slot (16).

17. An endoprosthesis as claimed claim 5, wherein said two condyle rolls (24) each have a bore (78) positioned eccentric to the center axis (22) of the condyle roll (24) for receiving said pin (14).

18. An endoprosthesis as claimed in claim 6, wherein a roller bearing (30) is arranged on said pin (14) in the opening (26) of the intracondylar cage (22) for guiding said pin in an elongated slot (16).

19. An endoprosthesis as claimed in claim 1, wherein rolling/sliding movement which takes place upon flexing of the joint is limited to a predeterminable flexion angle by means of the guide for said pin (14).

20. An endoprosthesis as claimed in claim 19, wherein said guide is formed as an elongated slot (16).

21. An endoprosthesis as claimed in claim 19, wherein said flexion angle is between 85 and 95 degrees in size.

* * * * *